(12) United States Patent
Ewing et al.

(10) Patent No.: US 8,267,886 B2
(45) Date of Patent: Sep. 18, 2012

(54) CATHETER HAVING A CORE WIRE AND A LOW PROFILE BOND

(75) Inventors: Benjamin T. Ewing, Wexford, PA (US); Gregory A. Brucker, Minneapolis, MN (US); Scott A. Bednar, Freedom, PA (US); John R. Periard, North Huntington, PA (US)

(73) Assignee: Medrad, Inc., Indianola, PA (US)

( * ) Notice: Subject to any disclaimer, the term of this patent is extended or adjusted under 35 U.S.C. 154(b) by 839 days.

(21) Appl. No.: 12/339,686

(22) Filed: Dec. 19, 2008

(65) Prior Publication Data
US 2009/0163891 A1    Jun. 25, 2009

Related U.S. Application Data

(60) Provisional application No. 61/015,422, filed on Dec. 20, 2007.

(51) Int. Cl.
*A61M 29/00* (2006.01)
*A61M 25/00* (2006.01)

(52) U.S. Cl. .................................... 604/96.01; 604/284

(58) Field of Classification Search .............. 604/96.01, 604/103, 523–528
See application file for complete search history.

(56) References Cited

U.S. PATENT DOCUMENTS

| | | | |
|---|---|---|---|
| 3,435,826 A | 4/1969 | Fogarty | |
| 4,650,466 A | 3/1987 | Luther | |
| 4,917,667 A | 4/1990 | Jackson | |
| 5,042,976 A | 8/1991 | Ishitsu et al. | |
| 5,324,263 A | 6/1994 | Kraus et al. | |
| 5,364,376 A * | 11/1994 | Horzewski et al. | 604/528 |
| 5,460,608 A * | 10/1995 | Lodin et al. | 604/103.09 |
| 5,545,134 A | 8/1996 | Hilaire et al. | |
| 5,554,118 A | 9/1996 | Jang | |
| 5,662,608 A | 9/1997 | Imran et al. | |
| 5,803,083 A * | 9/1998 | Buck et al. | 600/439 |
| 5,951,513 A | 9/1999 | Miraki | |
| 6,019,736 A * | 2/2000 | Avellanet et al. | 600/585 |
| 6,733,473 B1 * | 5/2004 | Reifart et al. | 604/96.01 |
| 6,800,065 B2 * | 10/2004 | Duane et al. | 604/96.01 |
| 2007/0016132 A1 | 1/2007 | Oepen et al. | |
| 2007/0282367 A1 | 12/2007 | Jeffrey et al. | |

FOREIGN PATENT DOCUMENTS

| | | |
|---|---|---|
| WO | 9320877 | 10/1993 |
| WO | 9729801 | 8/1997 |
| WO | 9904847 | 2/1999 |

* cited by examiner

*Primary Examiner* — Kevin C Sirmons
*Assistant Examiner* — Bradley Osinski
(74) *Attorney, Agent, or Firm* — David Schramm

(57) ABSTRACT

A catheter having a shaft that has at least two spaced-apart lumens is disclosed. A retractable core wire is disposed within at least one of the lumens. The retractable core wire is manipulated by the user to impart variable stiffness to the shaft as the core wire is retracted and extended within the lumen. A catheter having substantially low profile bonds at the junctions where an inflatable balloon is attached to the catheter is also disclosed. The low profile bonds are created by recesses extending around the circumference of the distal end of the shaft, the proximal and distal ends of a stem, and the proximal end of a tip. The catheter having the low profile bond optionally has either a retractable or an embedded core wire. In examples, the catheter has at least one component formed from, co-extruded with, or coated with a lubricious material or a hydrophilic material.

27 Claims, 15 Drawing Sheets

CATHETER HAVING A CORE WIRE AND A LOW PROFILE BOND

CROSS-REFERENCE TO RELATED APPLICATION

The present application claims priority to 61/015,422, filed Dec. 20, 2007.

BACKGROUND

The following background information is provided to assist the reader to understand the disclosure provided below and the environment in which embodiments of the disclosed catheter will typically be used. The terms used herein are not intended to be limited to any particular narrow interpretation unless clearly stated otherwise in this document.

Percutaneous transluminal angioplasty (PTA) is a medical procedure that is used to reduce or eliminate blockages within the vascular system in order to relieve clinical symptoms associated with reduced blood flow to an organ or region of the body. PTA works by placing a non-elastomeric balloon within a blockage and inflating it with sufficient force to enlarge stenotic lesions. The balloon compresses the atherosclerotic plaque to effectively enlarge a previously constricted lumen. This procedure has become a primary therapy for treatment of occlusive vascular disease.

A typical angioplasty interventional procedure starts with a puncture into the vascular system, usually in a femoral artery. Once access is gained, a first guidewire is placed through the center of the needle into the artery and the needle is removed. A sheath with a dilator of a given size, commonly called an introducer, is then placed over the guidewire into the artery to expand the puncture site and to maintain continuous access. The dilator and guidewire are then removed leaving the hemostasis valve of the introducer to seal against blood flow but allow access to the artery. A second guidewire and diagnostic catheter are then placed through the introducer into the vasculature with the guidewire going prior to the diagnostic catheter. Once the diagnostic catheter is placed over the second guidewire, that guidewire is removed and an injection of contrast fluid is usually done to visualize the peripheral vascular system and identify target lesions for revascularization. A third guidewire may be then inserted through the diagnostic catheter into the vascular system and positioned so the tip of the guidewire is distal to the target lesion. This guidewire protects the artery from damage as the balloon catheter traverses the vascular system after the diagnostic catheter has been removed. A balloon catheter is then flushed and the catheter tip loaded onto the guidewire after which the balloon catheter is inserted through the vascular introducer. The balloon catheter travels over the guidewire sometimes through rather tortuous vasculature and is positioned at the target lesion so that marker bands, which delineate the treatment area of the balloon, are positioned proximal and distal to the stenosis. A variable stiffness to this catheter can greatly enhance the ability of the interventionalist to traverse the vascular system and place the interventional catheter, in this case a balloon catheter, at the appropriate point for the procedure. The balloon is then inflated to the desired diameter and remains expanded for approximately one minute, after which it is deflated and the balloon catheter is removed from the vascular system. If additional procedures are necessary, the remaining guidewire functions to facilitate placement of any additional interventional devices. An injection of contrast is finally made to verify that the stenosis has been sufficiently dilated. Upon completion of the intervention, the guidewire and introducer are removed from the vascular system and the puncture wound sealed. The devices of the present disclosure utilize one or more retractable core wires within the balloon catheter to vary the stiffness of the catheter as it travels through a patient's vasculature.

SUMMARY OF THE INVENTION

In an embodiment, a core wire for use with a catheter is disclosed. The core wire comprises a substantially stiff member configured for retractable disposal into a lumen of a shaft of the catheter. Optionally, a tab is coupled to a proximal end or a proximal portion of the substantially stiff member to facilitate retraction or extension of the member within the lumen.

In various embodiments, a catheter adapted for insertion into a body vessel is disclosed. The catheter comprises a connector having an inflation channel and a guidewire channel; a shaft joined at a proximal end to the connector and having an inflation lumen that is in fluid communication with the inflation channel and an inflatable balloon; at least one core wire lumen containing a retractable core wire within each core wire lumen; a guidewire lumen configured for disposition of a guidewire therein and in fluid communication with the guidewire channel; a stem around which the inflatable balloon is positioned; and a flexible tip.

In another embodiment, a catheter is disclosed. The catheter comprises at least one retractable core wire; a first tubular member having a lumen, a proximal end configured for connection with a connector, a distal end configured for connection with an inflatable balloon, and a length defined by proximal and distal ends; at least one second tubular member having a lumen configured for disposal of the retractable core wire therein; a third tubular member having a lumen configured for disposal of a guidewire therein; and a sheath binding the tubular members.

In another embodiment, a catheter having low profile bonds is disclosed. The catheter comprises a shaft having a first recess that extends around a circumference of a distal portion of the shaft; a stem having a second recess that extends around a circumference of a proximal portion of the stem and a third recess that extends around a circumference of a distal portion of the stem, wherein the first and second recesses are substantially flush to form a first junction; a tip having a fourth recess that extends around a circumference of a proximal portion of the tip, wherein the third and fourth recesses are substantially flush with each other to form a second junction; an inflatable balloon positioned substantially around the exterior of the stem and having proximal and distal ends, wherein the proximal end is adhered substantially in the first junction and wherein the distal end is adhered substantially in the second junction, and wherein the junctions have substantially low profile bonds.

In additional embodiments, at least one of the shaft, stem, lumens, tubular members, core wire, and tip is at least one of formed from, co-extruded with, and coated with a lubricious material or a hydrophilic material.

In another embodiment, a method of using a catheter having a retractable core wire is disclosed, the method having the steps of: advancing the guidewire in a distal direction within a vessel to a target site in the vessel; advancing the catheter over the guidewire in a distal direction by inserting the guidewire into the guidewire lumen to a tortuous region within the vessel; retracting the retractable core wire in a proximal direction within the core wire lumen to adjust the stiffness of the shaft, wherein the stiffness of the shaft facilitates movement of the shaft through the tortuous region.

Optionally, the retractable core wire is then extended in a distal direction within the core wire lumen. In optional steps, the retractable core wire is removed from the core wire lumen and/or is reinserted into the core wire lumen.

Those and other details, objects, and advantages of the present disclosure will become better understood or apparent from the following description and drawings showing embodiments thereof.

BRIEF DESCRIPTION OF THE FIGURES

The accompanying drawings illustrate examples of embodiments of the disclosed catheter. In such drawings.

DESCRIPTION

Figure 1:
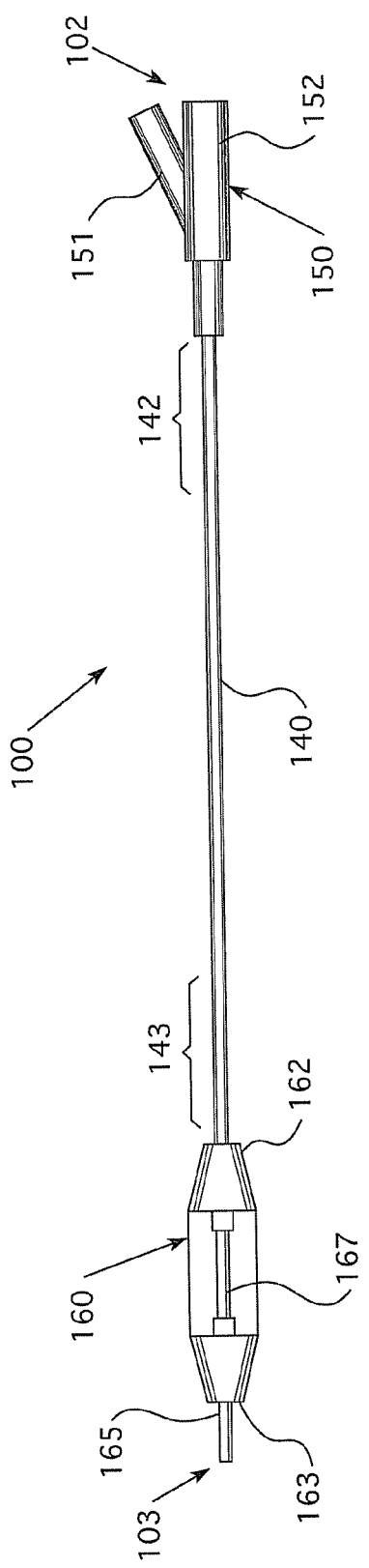
FIG. 1 is a side view of an embodiment of a catheter in its fully assembled state.

FIG. 1 is a side view of an embodiment of a catheter 100 in its fully assembled state. The catheter 100 is adapted for insertion into a body vessel to reduce or eliminate blockages within the vascular system in order to relieve clinical symptoms associated with reduced blood flow to an organ or region of the body. The catheter 100 is, for example, an over-the-wire catheter or a rapid exchange catheter 100. In examples, the catheter 100 is a coaxial design on an over-the-wire platform, (see, e.g., FIG. 9) or a multi-lumen design on an over-the-wire platform (see, e.g., FIGS. 5-8). The catheter 100 has distal 103 and proximal ends 102. See FIG. 1. As used herein, the terms "proximal" and "distal" are used to indicate relative positions along the catheter 100, with the proximal end 102 of the catheter located on the right of FIG. 1 and the distal end 103 of the catheter located on the left of FIG. 1. The catheter 100 comprises a shaft 140 joined at its proximal end 142 to a connector 150 that facilitates access to a lumen of the shaft 140, thereby enabling the user to position the catheter 100 in the vessel at a target site, and at its distal end 143 to an inflatable balloon 160 that is inflated to reduce or eliminate blockages. A tab 175 that is connected to or mounted on a retractable core wire 170 (see, e.g., FIGS. 2, 10, and 11) is configured for manipulation by the user to impart maximal stiffness to the shaft 140 when the retractable core wire 170 is fully extended in a distal direction and to provide more flexibility to the shaft 140 when the retractable core wire 170 is retracted in a proximal direction. The retractable core wire 170 permits the user to adjust the stiffness of the shaft 140 to facilitate insertion of the catheter 100 through the vessel based, for example, on the degree of restenosis or tortuosity of the vessel. In examples, the catheter 100 has more than one retractable core wire 170. See FIGS. 6, 7, and 12. In the figures (see, e.g., FIGS. 2 and 3), the inflatable balloon 160 is generally shown in the inflated state. Optionally, the inflatable balloon has marker bands (not shown) to delineate the treatment area of the balloon. In an example, such as the one shown in FIG. 1, the catheter 100 further comprises a stem 167 around which the balloon is positioned and a tip 165 that guides the catheter 100 in the vessel and that is configured to minimize trauma to the vessel. Optionally, the tip 165 is flexible. The catheter further comprises a guidewire 190 configured for disposition within a lumen of the catheter to facilitate insertion of the catheter through the vessel. See FIG. 2.

Figure 2:
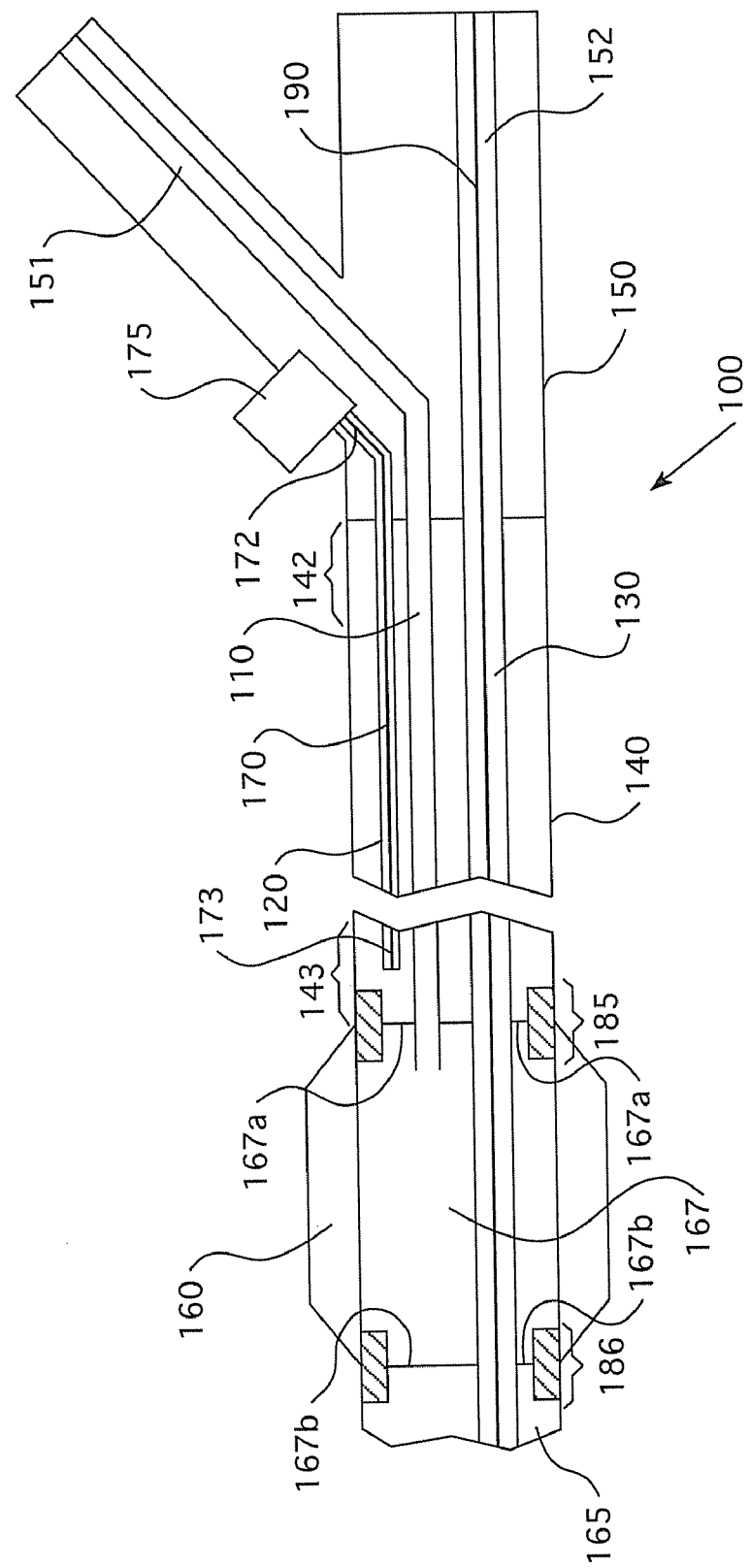
FIG. 2 is a view of a longitudinal section of an embodiment of a catheter having a retractable core wire connected to a tab and low profile bonds at which an inflatable balloon attaches to recessed areas on the shaft, stem, and tip.
Figure 3:
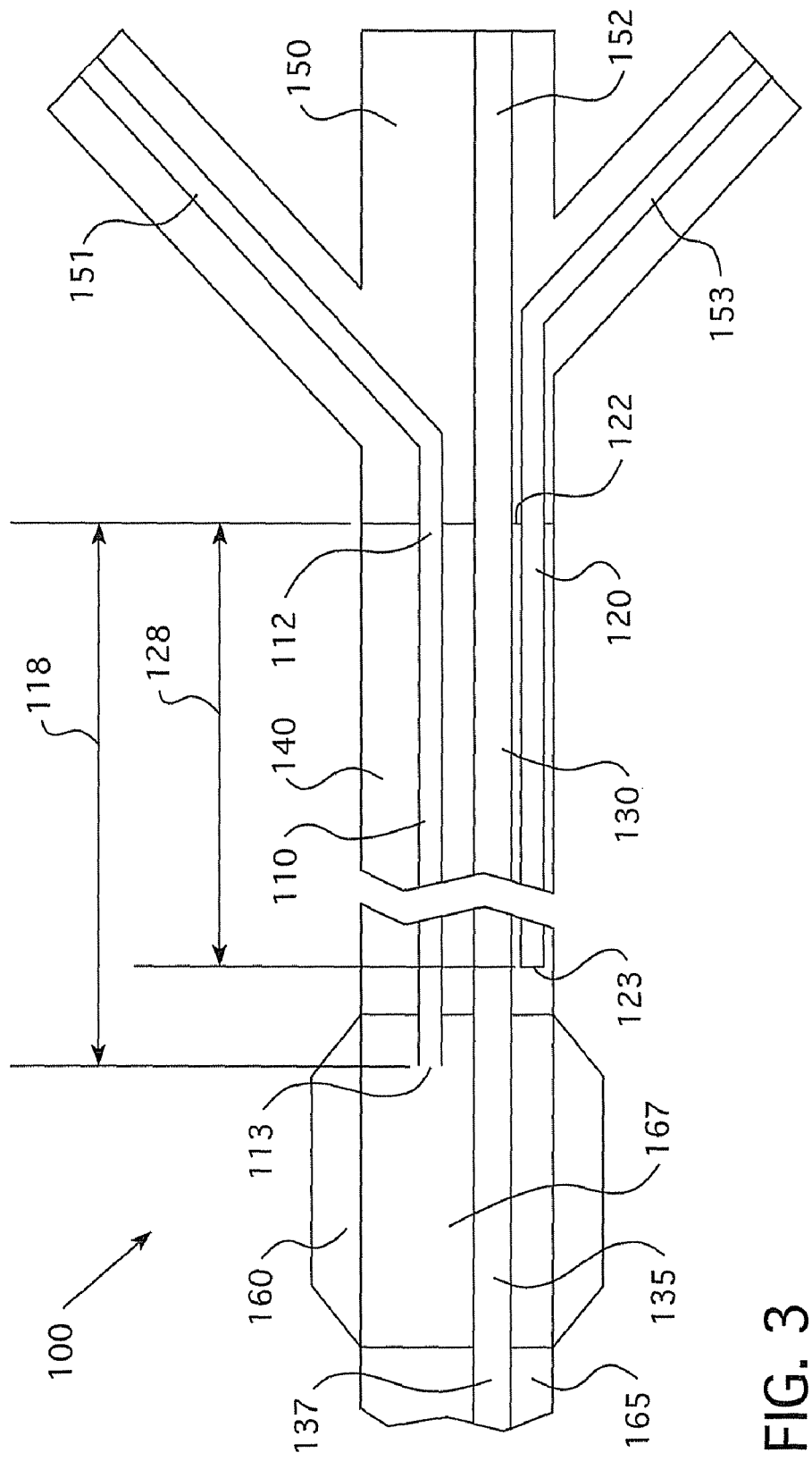
FIG. 3 is a view of a longitudinal section of an embodiment of a catheter having a connector having three channels.
Figure 4:
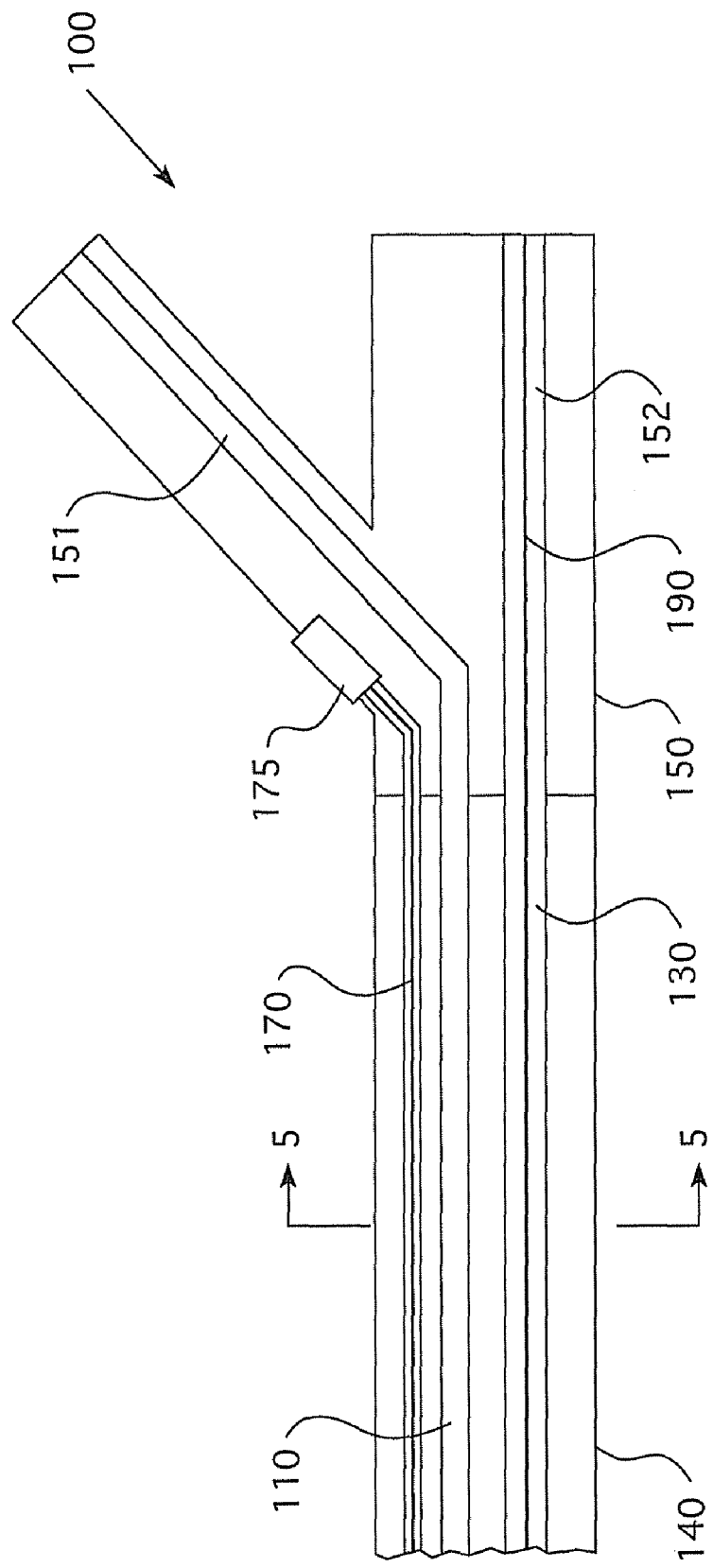
FIG. 4 is a view of a longitudinal section of an embodiment of a catheter having a retractable core wire connected to an integrated tab.

In examples, the shaft 140 of the catheter 100 is either extruded or molded. FIGS. 2 and 3 provide sectional views of embodiments of the catheter 100. As shown, the shaft 140 has proximal and distal ends 142, 143 and a length that is defined by the ends 142, 143. The shaft 140 has dimensions appropriate for ease of handling, with the diameter being such that it minimizes trauma to the vessels and tissue and allows for tracking to small vessels while also maintaining structural integrity and allowing passage of the guidewire 190. The length is sufficient to extend from a point of entry into the vessel along the length of the vessel to the target site, such as an area of stenosis. In an example, the shaft 140 is at least one of made from, co-extruded with, and coated with a hydrophilic material or a lubricious material such as, for example, nylon, Rilsan® nylon, polytetrafluoroethylene (PTFE), PEBAX® material, polyether ether ketone (PEEK), polyimide, polyethylene of varying densities, polyethylene (PE), polyethylene terephthalate (PET), polyurethane (PU), high density PE (HDPE), or fluorinated ethylene propylene, alone, in combination, or in multilayers.

Figure 5:
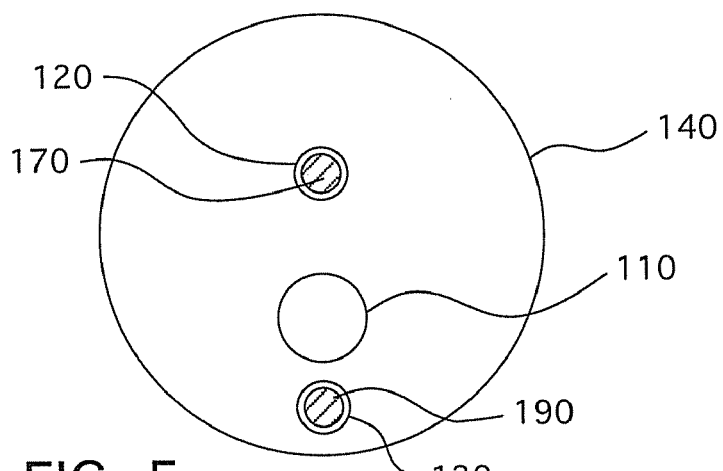
FIG. 5 is a cross-sectional view at line 5-5 of the catheter of FIG. 4.
Figure 6:
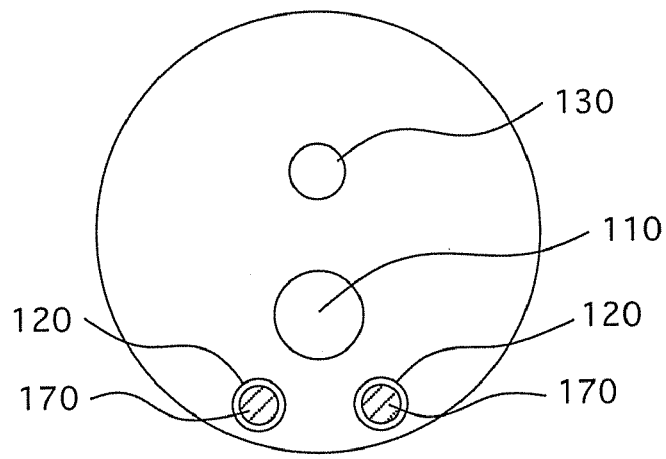
FIG. 6 is a cross-sectional view of an embodiment of a catheter having two retractable core wires and an inflation lumen.
Figure 7:
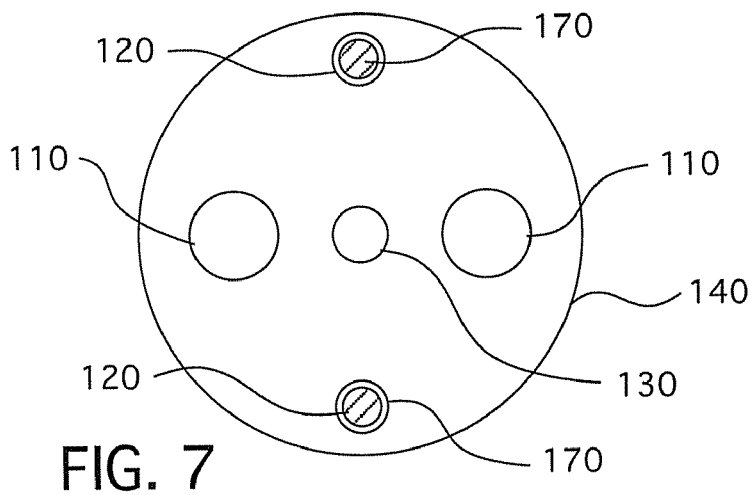
FIG. 7 is a cross-sectional view of an embodiment of a catheter having two inflation lumens and two retractable core wires.
Figure 8:
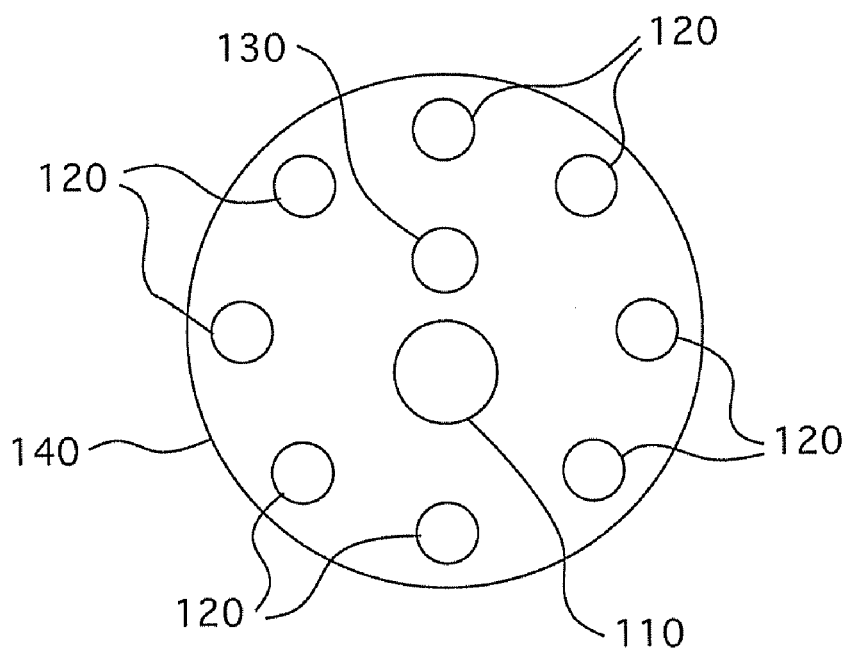
FIG. 8 is a cross-sectional view of an embodiment of a catheter having a plurality of retractable core wires disposed in lumens concentrically positioned around the inflation lumen.

The shaft 140 has at least one inflation lumen 110 having a length 118 defined by its proximal and distal ends 112, 113 and is configured at its proximal end 112 for fluid communication with an inflation channel 151 of the connector 150 and at its distal end 113 for communication with an inflatable balloon 160. See FIG. 3. The distal end 113 of the inflation lumen 110 extends into and is positioned substantially within the inflatable balloon 160 such that when saline, contrast dye, or a gas is infused through the lumen the balloon 160 is inflated. See FIG. 3. In examples, the inflation lumen 110 is positioned substantially centrally within the shaft 140, as shown in FIGS. 2 and 8. In other examples, the inflation lumen 110 is off-set from the central longitudinal axis of the shaft, as shown in FIGS. 5-7, and 9. In examples, the diameter of the lumen 110 is sized in proportion to the time that it takes for the balloon 160 to inflate or deflate. Optionally, the shaft 140 has more than one inflation lumen 110, as shown in FIG. 7, in order to, for example, provide more than one lumen that extends into and is positioned within the balloon 160, so as to increase or decrease inflation time or to provide more than one route of administration for various agents such as the contrast dye and saline. In an example, the inflation lumen 110 is at least one of formed from, co-extruded with, and coated with a hydrophilic material or lubricious material such as one of those listed above, including but not limited to Rilsan® nylon or PTFE.

Figure 17:
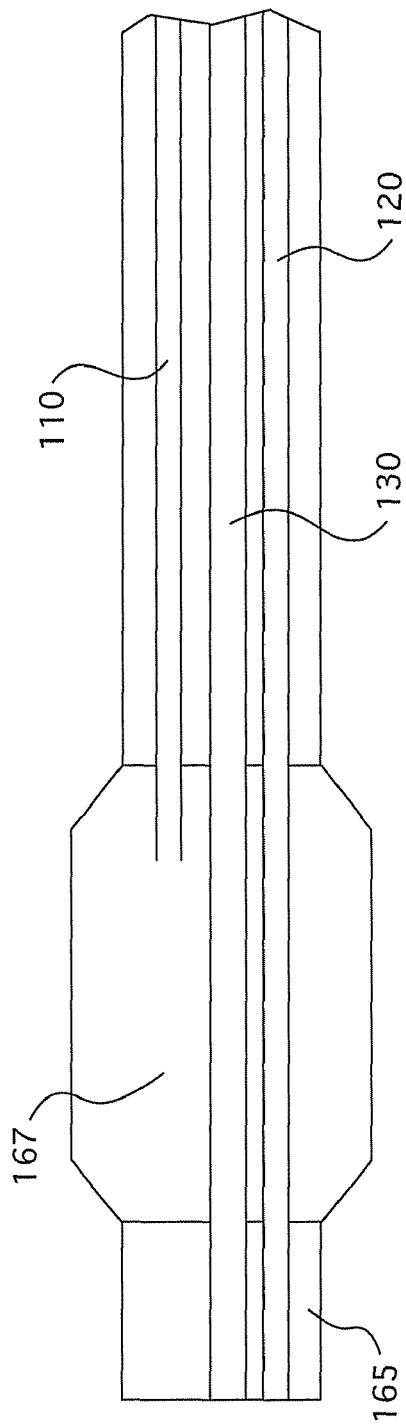
FIG. 17 is a longitudinal view of a section of an embodiment of a catheter having a core wire lumen extending through the stem and into the tip of the catheter.
Figure 18:
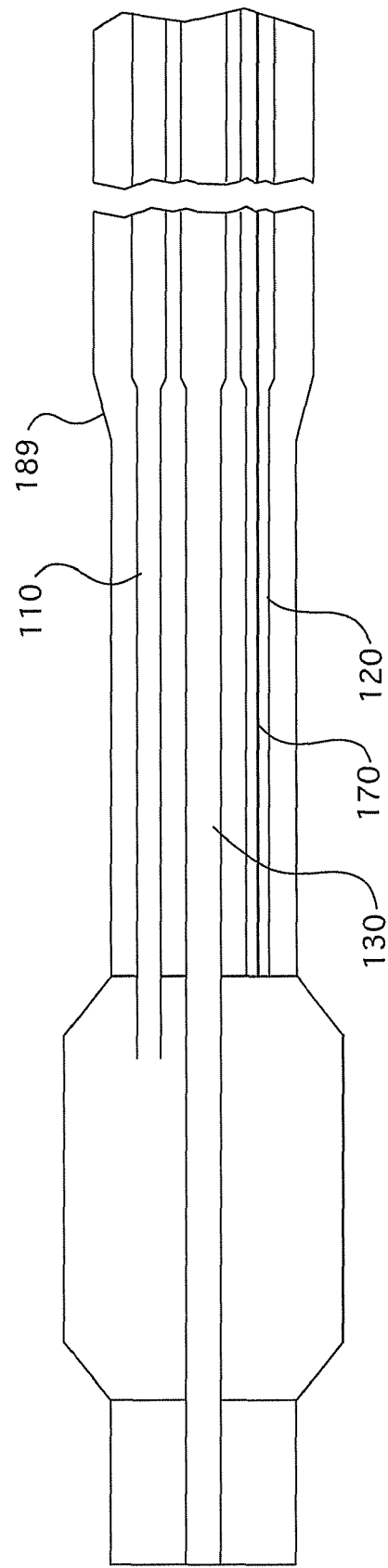
FIG. 18 is a longitudinal view of a section of an embodiment of a catheter having a tapered shaft.

As shown in FIGS. 2 and 3, the shaft 140 has a core wire lumen 120 that is configured for disposition of the retractable core wire 170 (described below) therein. Optionally, there is more than one core wire lumen 120. See, e.g., FIGS. 6-8. The core wire lumen 120 has a length 128 that is defined by distal and proximal ends 123, 122. In one example, the core wire lumen 120 has a length 128 that is less than the length of the shaft 140 of the catheter 100. See FIG. 3. In another example not shown, the core wire lumen 120 has a length 128 that is substantially equal to the length of the shaft 140 of the catheter 100. In other examples, the core wire lumen 120 has a length 128 that extends at least partially into the stem portion, through to the tip portion, or a variation thereof. See FIG. 17. The core wire lumen 120 has an inner diameter that is greater than the outer diameter of retractable core wire 170 and is sized to facilitate retraction and extension of the retractable core wire 170 therein. In examples, the core wire lumen 120 is substantially elongate (see FIG. 17), substantially tapered (see FIG. 18), or substantially helical (not shown). In an example, the core wire lumen 120 is at least one of formed from, co-extruded with, and coated with a hydrophilic material or at least one of the lubricious materials listed above such as Rilsan® nylon or PTFE. The core wire lumen 120 is positioned relative to the inflation lumen 110 in any number of configurations, but in an example is centrally positioned. See FIG. 5. In the examples shown in FIGS. 5 through 9, the core wire lumen 120 is positioned laterally to the inflation lumen 110. In use, such an arrangement enables directional flexibility. In the example shown in FIG. 8, a plurality of core wire lumens 120 is concentrically positioned around a substantially centrally positioned inflation lumen 110. In an alternate embodiment, the core wire may be fixed.

Figure 9:
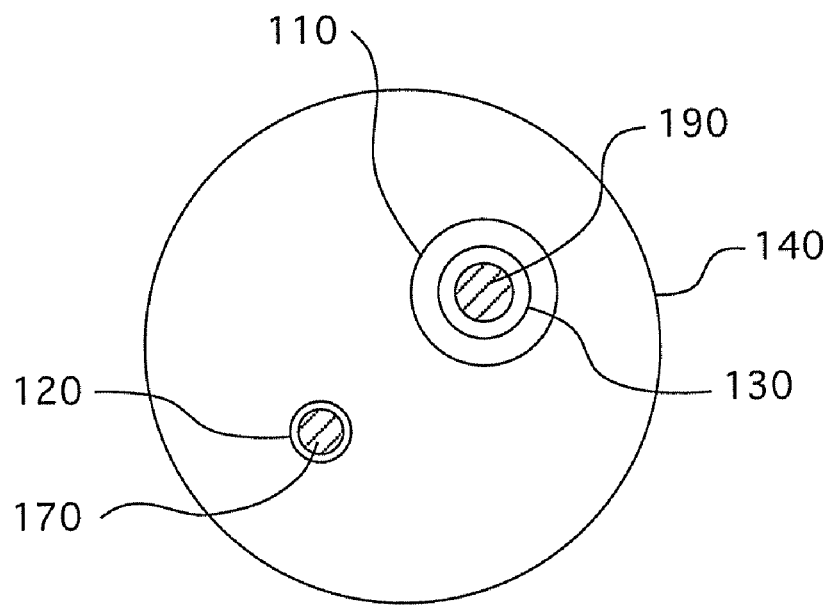
FIG. 9 is a cross-sectional view of an embodiment of a catheter having a retractable core wire positioned parallel to the inflation lumen and the guide wire positioned coaxially in the inflation lumen.

As shown in FIGS. 2 and 3, the shaft 140 has a guidewire lumen 130 having proximal and distal ends that define a length and that is configured for disposition of a guidewire 190 (described below) therein. The guidewire lumen 130 is sized to facilitate retraction and extension of the guidewire 190 therein. The guidewire lumen 130 extends the length of the shaft 140 and is in fluid communication with a guidewire lumen of the stem 167 portion that is in fluid communication with a guidewire lumen of a flexible tip 165 portion. Optionally, the guidewire lumen 130 is positioned coaxially within the inflation lumen 110, as shown in FIG. 9. In another example, the guidewire lumen 130 is substantially parallel to at least one of the inflation and core wire lumens 110, 120. See FIG. 5.

In an embodiment, the shaft 140 may be tapered 189 over a defined portion of the length. See FIG. 18. In an example, the shaft tapers two-thirds of the distance toward the distal end. In other examples, the tapered shaft 140 may have substantially elongate lumens (not shown), at least one tapered lumen, or a plurality of tapered lumens (see, e.g., FIG. 18).

As shown, a connector 150 is positioned at the proximal end 142 of the shaft 140 and has at least one channel 151, 152, 153. See FIGS. 2-4 and 10-12. In the examples shown, an inflation channel 151 is in fluid communication with the inflation lumen 110 of the shaft 140 and is configured to receive an administration of fluids such as contrast dye and saline or a gas so that the user is able to control infusion to inflate the balloon 160. A guidewire channel 152 is configured to receive the guidewire 190 (described below) and is in communication with the guidewire lumen 130 of the shaft 140. Optionally, as shown in FIG. 3, a core wire channel 153 is configured to receive a retractable core wire 170 (described below) and is in communication with the core wire lumen 120 which is configured for disposition of the retractable core wire 170 therein. Optionally, there is more than one core wire channel 153 (not shown).

In an example, the retractable core wire 170 comprises a substantially stiff member configured for retractable disposition in the core wire lumen 120. As shown in FIGS. 2 through 10 and FIG. 12, the substantially stiff member of the retractable core wire 170 is disposed substantially concentrically within the core wire lumen 120. Optionally, there is more than one retractable core wire 170 each disposed within one of a plurality of core wire lumens 120. (See FIGS. 6-8, 12). The member of the core wire 170 has proximal and distal ends 172, 173 and a length defined by the ends 172, 173. See FIG. 2. In an example, the length of the member is substantially equal to the length 128 of the core wire lumen 120. See FIG. 3. In other examples, the length of the member of the core wire 170 is extended within the core wire lumen 120 at least partially through the stem 167 or the tip 165. For example, see FIG. 17.

Figure 19A:
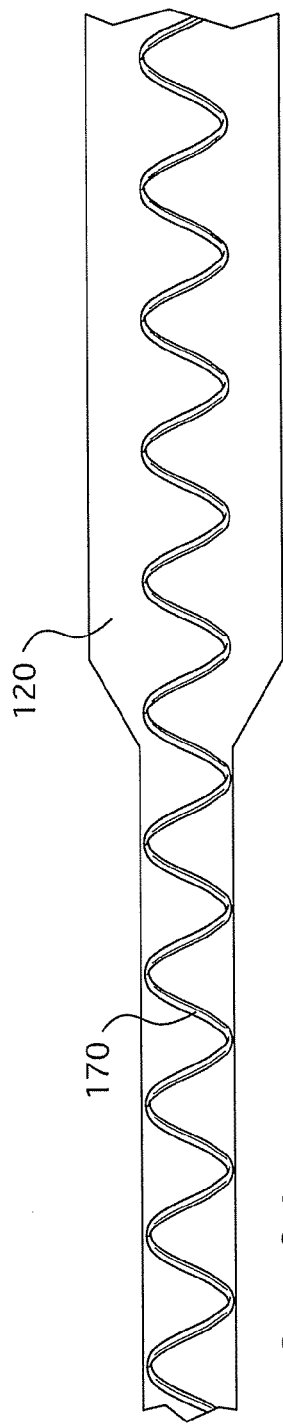
FIG. 19 shows enlarged longitudinal views of embodiments of a catheter having a helical core wire (FIG. 19A), a tapered core wire (FIG. 19B), and a coiled core wire (FIG. 19C).
Figure 19B:
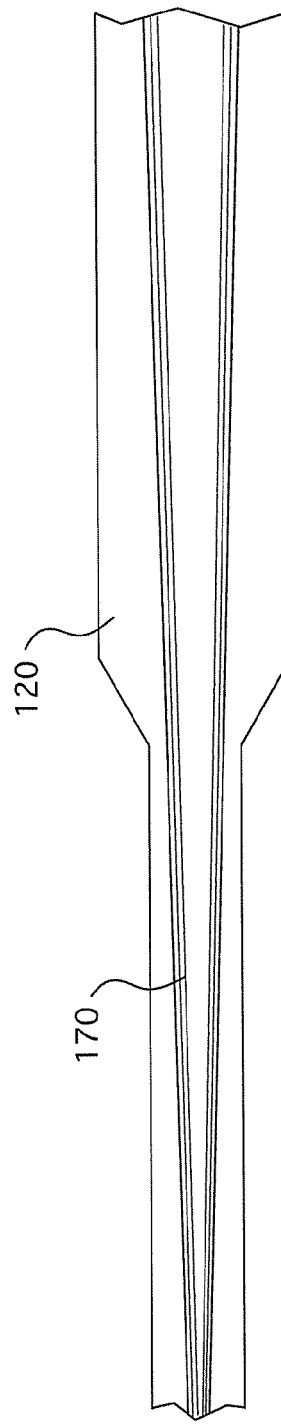
Figure 19C:
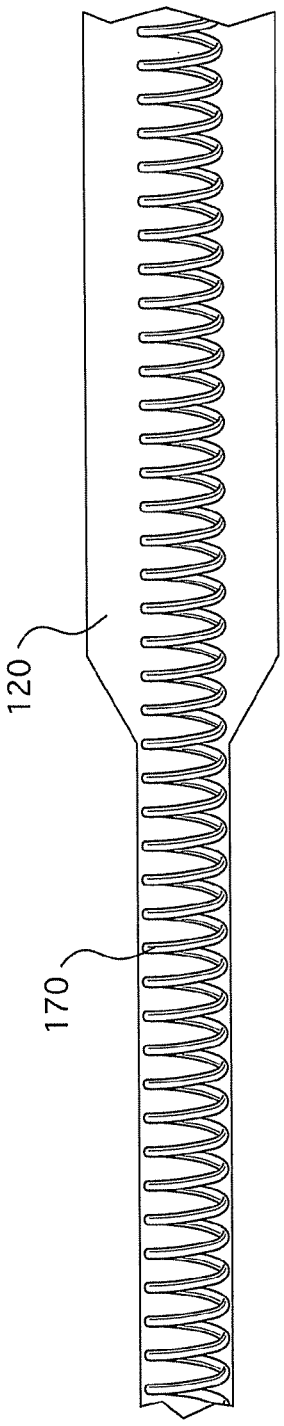

The member of the core wire 170 has an outer diameter that is less than an inner diameter of the core wire lumen 120. In examples, the member of the core wire 170 is at least one of substantially elongate (see FIG. 4), substantially helical (see FIG. 19A), substantially tapered to provide varied stiffness along an axial length (see FIG. 19B), or substantially coiled (see FIG. 19C) and having a solid tapered inner core (not shown). The member of the retractable core wire 170 generally has a substantially circular cross-section (not shown). In examples, the member has a diameter of about 0.010 inches to about 0.025 inches. In other examples, the member has a diameter that is smaller than about 0.010 inches, particularly in catheters having more than one retractable core wire 170. In another example, the member is substantially tapered over a defined portion of the length such as toward the distal end. The member of the retractable core wire 170 is made from, for example without limitation, stainless steel, nitinol, plastic, such as polyurethane, or a combination thereof and is optionally co-extruded with or coated with a hydrophilic material or a lubricious material such as those listed above, for example Rilsan® nylon or PTFE, or a hydrophilic material. In examples, the member of the core wire 170 is a mixture, overlay, or transition of at least two materials, such as stainless steel bonded to plastic.

The retractable core wire 170 is configured for extension within the core wire lumen 120 in the distal direction and for retraction within the core wire lumen 120 in the proximal direction. Optionally, the retractable core wire 170 is removable from the catheter 120, as shown, for example, in FIG. 11 and described in more detail below. The retractable core wire 170 imparts on the shaft 140 a stiffness that can be varied or manipulated. The stiffness of the shaft 140 is determined by the number of retractable core wires 170 within the shaft 140, the distal to proximal position of each retractable core wire 170 within the core wire lumen 120, the diameter of the member of the retractable core wire 170, the material from which the member comprising the retractable core wire 170 is made, and the position of the core wire lumen 120 into which the retractable core 170 wire is disposed relative to the inflation lumen 110. For example, the proximal portion of the core wire 170 is stiffer than the distal portion.

As shown in FIGS. 2, 4, and 10-12, in examples, the retractable core wire 170 has a tab 175 coupled to the proximal end 172 or a proximal portion of the substantially stiff member of the core wire 170 that facilitates retraction of the substantially stiff member within the core wire lumen 120. In one embodiment shown in FIGS. 2 and 4, the tab 175 is an integral portion of the connector 150 such that the tab 175 is removably positioned within the connector 150. The connector 150 has a slit 179 or an opening (see FIGS. 10 and 11) through which the substantially stiff member of the core wire 170 is inserted into and removed from the core wire lumen 120 of the shaft 140.

Figure 10:
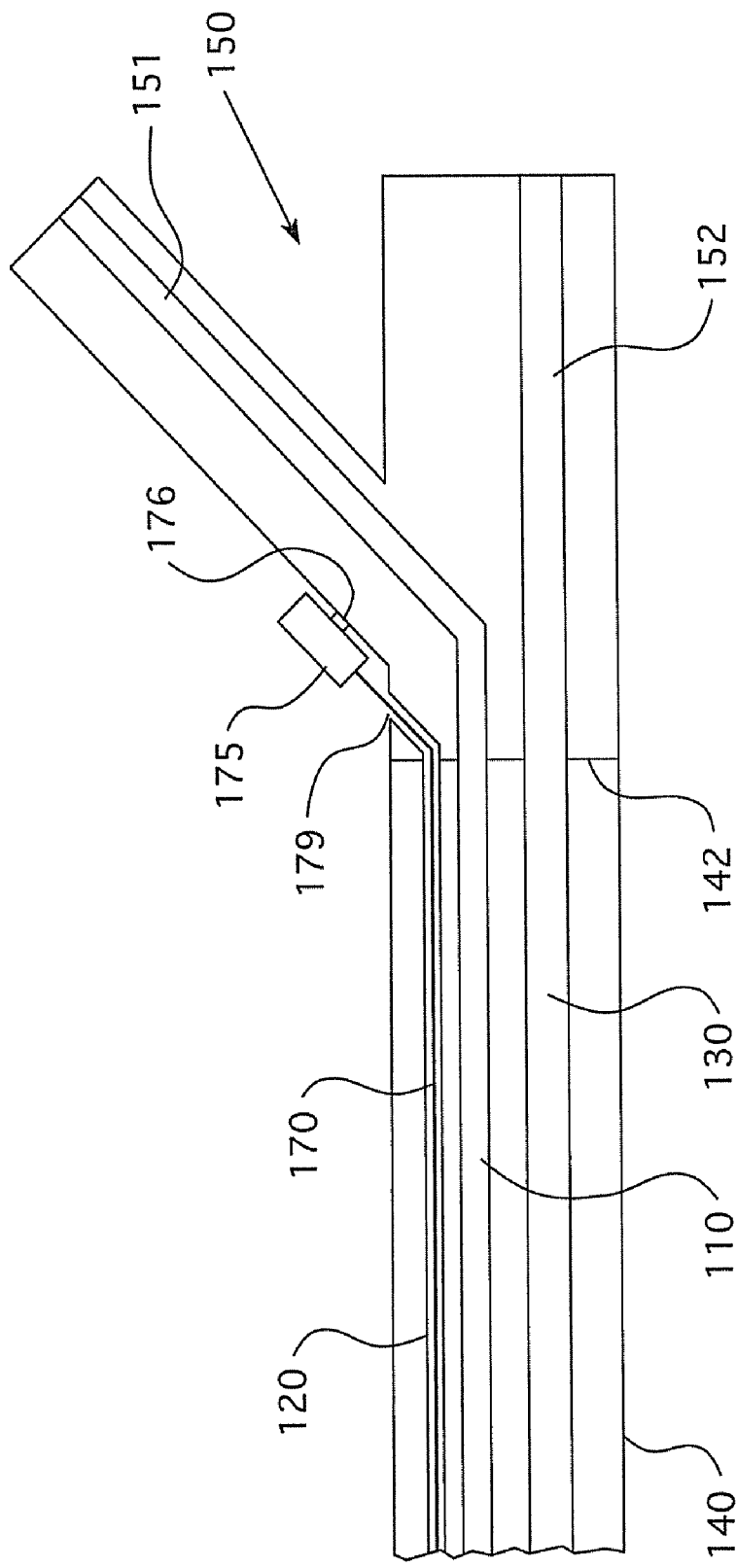
FIG. 10 is a longitudinal view of a section of an embodiment of a catheter having a retractable core wire connected to a detachable tab.

In another embodiment shown in FIG. 10, the tab 175 is a detachable or breakaway tab that is detachably mounted to the connector 150 by a detachable member 176. When the detachable member 176 is in-tact, the retractable core wire 170 is substantially stationary within the core wire lumen 120. When the detachable member 176 is detached from the connector 150, the retractable core wire 170 is able to be freely extended and retracted within the core wire lumen 120, for example by manipulating the tab 175 to control movement of the retractable core wire 170 within the core wire lumen 120. In use, the tab 175 is detached from the connector 150 by twisting or bending the detachable member 176, for example.

Figure 11:
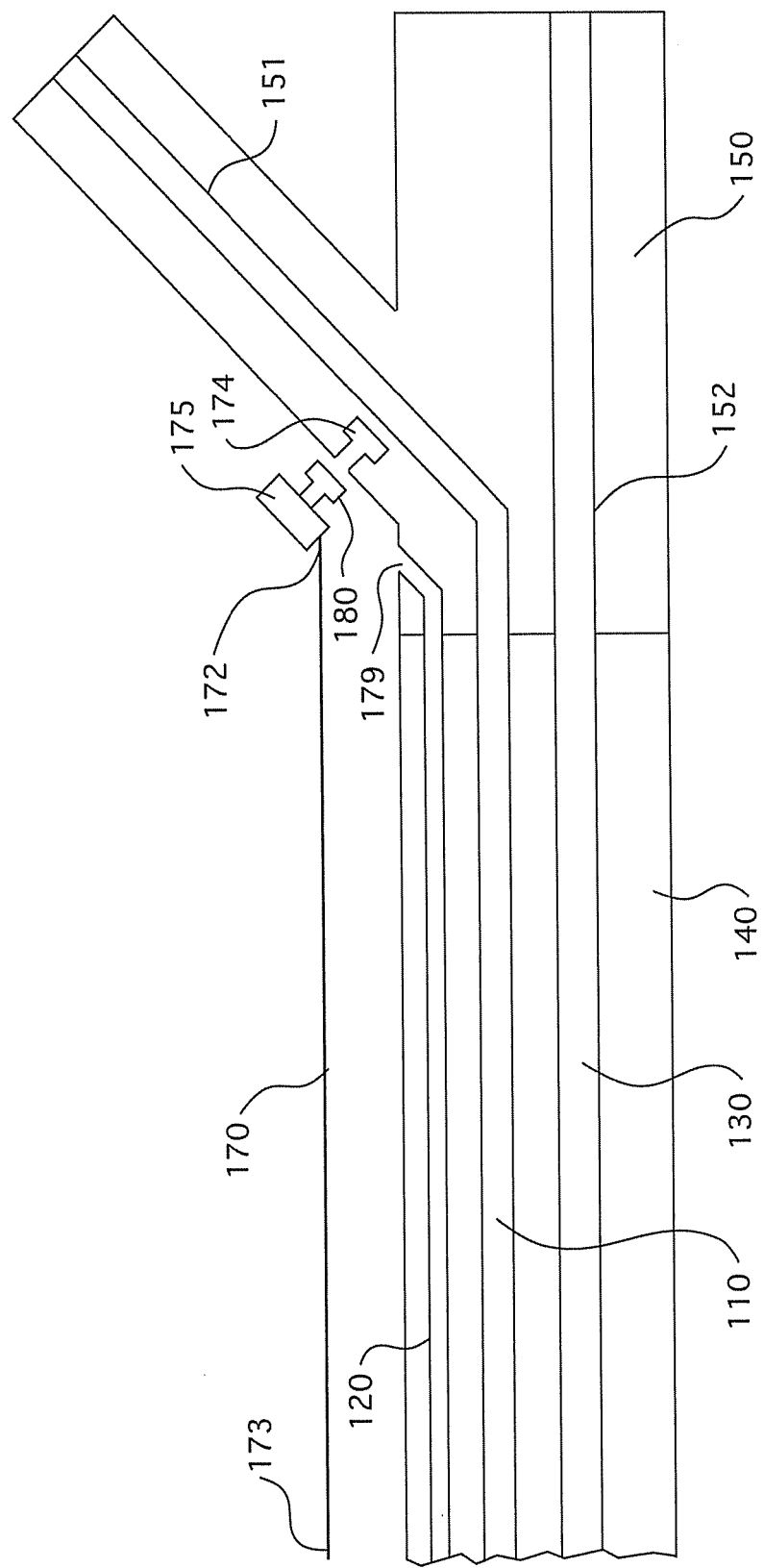
FIG. 11 is a side view of a schematic of an embodiment of a catheter having at least one removable core wire having a tab.
Figure 12:
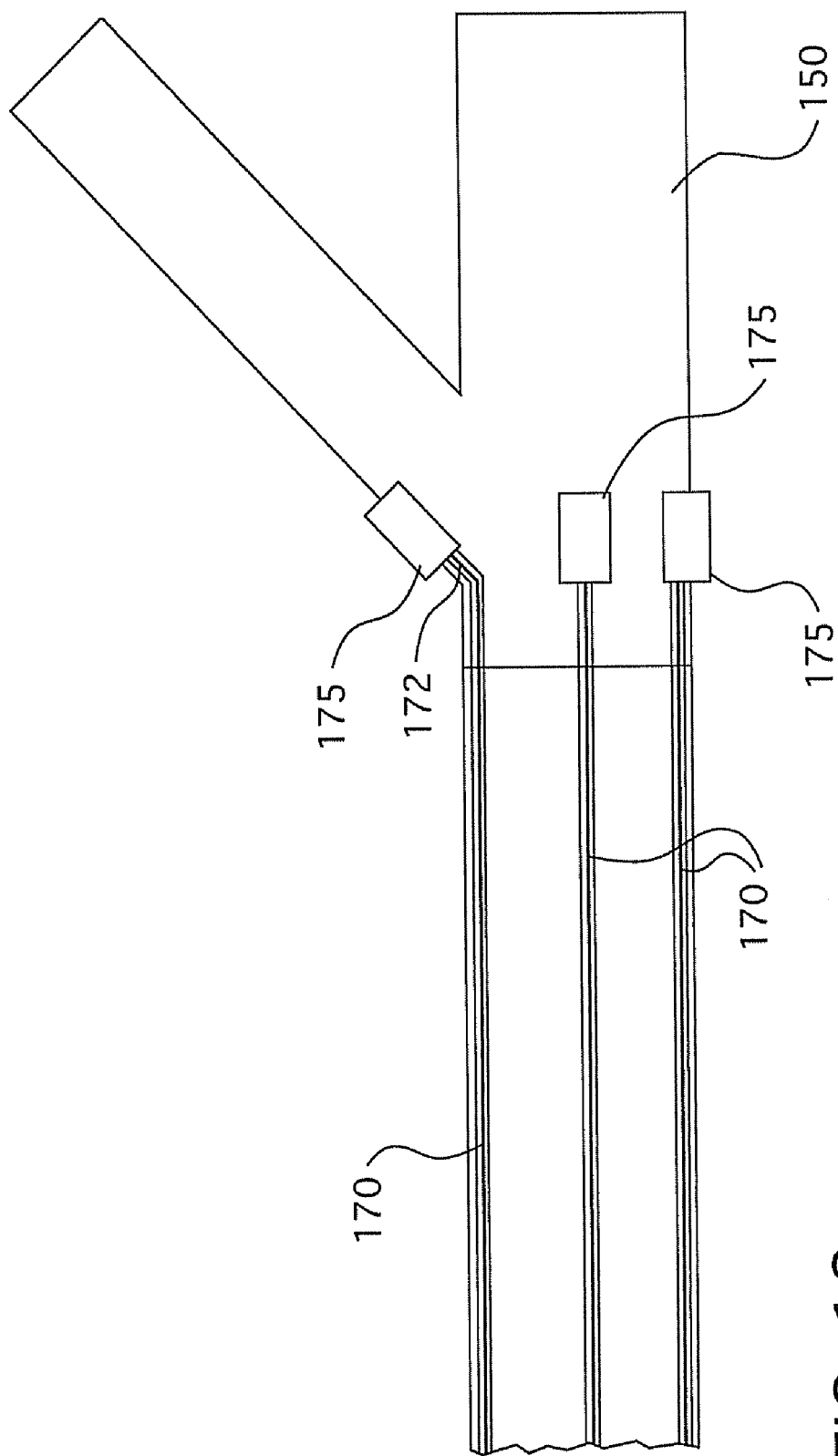
FIG. 12 is a side view of a schematic of an embodiment of a catheter having a plurality of retractable core wires, each core wire having a tab.

In another embodiment shown in FIG. 11, the tab 175 is configured for insertion into a slot located in the connector 150. In the example shown, the tab 175 has a member that is any of a variety of shapes, such as a T-shaped member 180 shown in FIG. 11 that is configured for insertion into a substantially complimentary shaped slot in the connector, such as the T-shaped slot 174 shown in FIG. 11. A slit 179 or an opening (not shown) in the connector 150 provides access to the core wire lumen 120 for insertion or removal of the substantially stiff member of the retractable core wire 170. When the tab 180 is inserted into the slot 174, the retractable core wire 170 is disposed within the core wire lumen 120. When the tab 180 is removed from the slot 174, the retractable core wire 170 can be removed from the core wire lumen 120 and/or manipulated in order to vary the stiffness of the catheter 100.

Optionally, the catheter 100 has more than one retractable core wire 170. In the example shown in FIG. 12, the catheter 100 has a plurality of retractable core wires 170, with each core wire 170 having a tab 175 coupled to the proximal end 172 or portion of the stiffening member of the core wire 170.

As discussed above, the guidewire lumen 130 is configured for disposition of a guidewire 190 that is used for maneuvering the catheter 100 to the desired location within the vessel. See FIG. 2. The guidewire 190 has a cross-section that is generally circular and has an outer diameter that is smaller than an inner diameter of the guidewire lumen 130 into which it is disposed. The guidewire 190 is any length that is suitable for a given procedure, but in one embodiment is about 300 cm in length. In examples, the outer diameter of the guidewire is about 0.012 inches to about 0.038 inches. In examples, the guidewire 190 is made from nitinol or stainless steel and is optionally coated with urethane or a hydrophilic coating. In an example, the guidewire 190 is positioned within the connector 150, such as within the guidewire channel 152 of the connector 150, as shown in FIGS. 2 and 3. The positioning of the guidewire 190 within the connector 150 makes the guidewire 190 accessible to users for manipulation of the guidewire 190 along the length of the vessel. In the example shown in FIG. 2, the lumen 130 for the guidewire 190 is positioned in the shaft 140 parallel to the inflation lumen 110. FIG. 5 shows a cross-sectional view of the catheter 100 shown in FIG. 4 at line 5-5, showing the guidewire 190 positioned substantially concentrically within the guidewire lumen 130, with the guidewire lumen 130 being positioned parallel with the inflation lumen 110.

Figure 13:
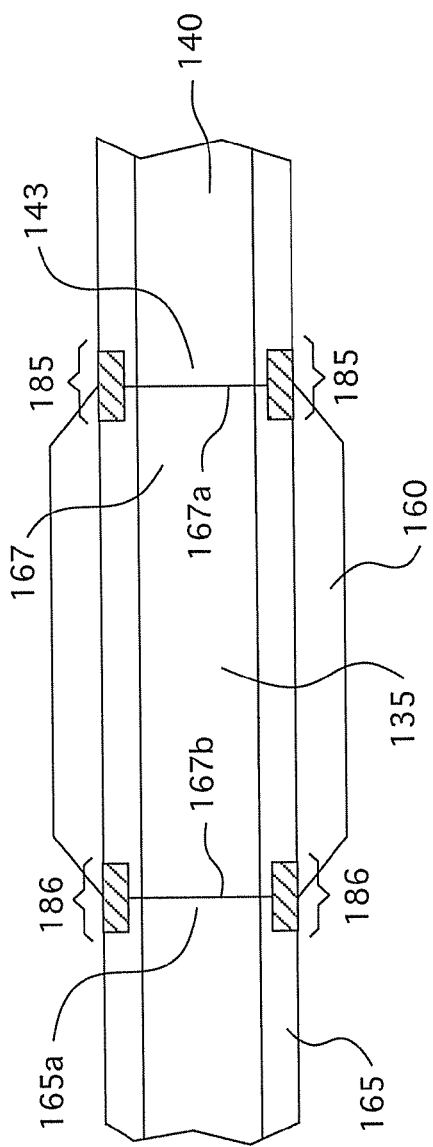
FIG. 13 is a longitudinal view of a section of an embodiment of a catheter having low profile bonds created by recesses that extend around the circumference of a distal portion of the shaft, the proximal and distal portions of a stem, and the proximal portion of a tip at the junctions where an inflatable balloon is attached.

As shown in FIGS. 2, 3, and 13, the catheter 100 is further comprised of a stem 167 having proximal and distal ends 167a, 167b and portions, wherein the proximal end 167a is connected to the distal end 143 of the shaft 140 and the distal end 167b is connected to the proximal end 165a of a tip 165. See FIG. 13. A stem guidewire lumen portion 135 is configured for disposition of the guidewire 190 therein and in fluid communication with the guidewire lumen 130. See FIG. 3. The tip 165 is comprised of proximal and distal ends and has a tip guidewire lumen portion 137 configured for disposition of the guidewire 190 therein and in fluid communication with the stem guidewire lumen portion 135. As such, the guidewire lumen is continuous throughout the length of the catheter 100.

Figure 14:
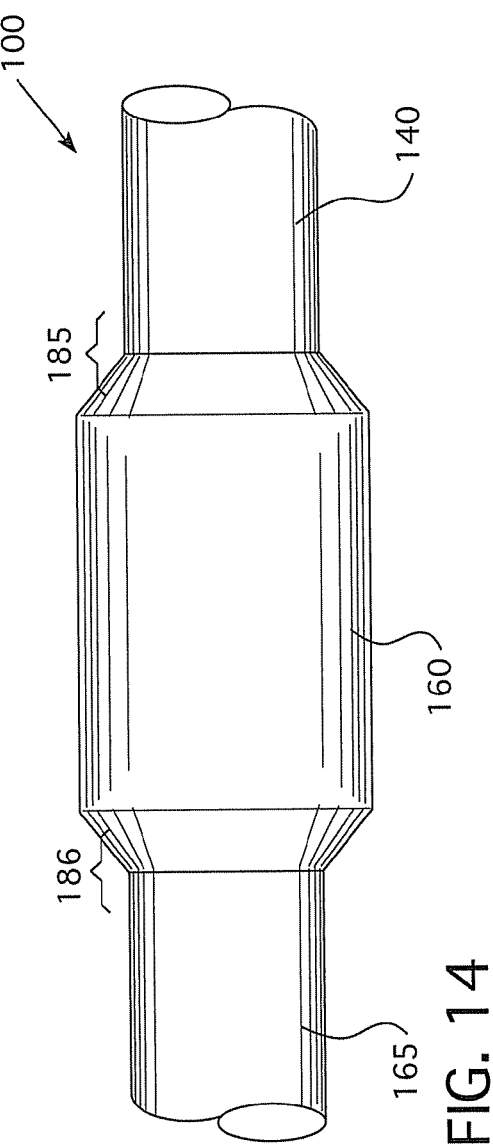
FIG. 14 is a side view of a schematic of an embodiment of a catheter having low profile bonds created by recesses that extend around the circumference of a distal portion of the shaft, the proximal and distal portions of a stem, and the proximal portion of a tip at the junctions where an inflatable balloon is attached.

In another embodiment shown in FIGS. 2, 13, and 14, the catheter 100 has low profile bonds at the junctions where the inflatable balloon 160 is attached. Optionally, the catheters 100 having the low profile bonds have at least one retractable core wire 170 such as those described herein or an embedded or fixed core wire (not shown). The low profile bonds 185, 186 are created by recesses that extend around a circumference of a distal portion of the shaft 140, the proximal and distal portions of the stem 167, and a proximal portion of the tip 165. The recesses of the shaft and the proximal portion of the stem are substantially flush with each other creating a first junction where the proximal end of the inflatable balloon 160 is attached, thereby creating the low profile bond 185. The recesses of the distal portion of the stem 167 and the proximal portion of the tip 165 are substantially flush with each other creating a second junction where the distal end of the inflatable balloon 160 is attached, thereby creating a second low profile bond 186. In an example, the low profile bond is a substantially zero profile bond that creates a substantially uniform profile over the entire length of the catheter 100 at the junctions.

In an example, the recesses are formed by extruding the recess in the components. In another example, the recesses are accomplished by post-processing, such as by mechanically creating the recesses using for example and without limitation heat, grinding, laser, or pressure.

In use, the guidewire is inserted into the vascular system. The guidewire 190 is inserted into the tip 165 and the corresponding lumens of the stem and shaft are advanced over the guidewire 190 in a distal direction until the tip 165 reaches a tortuous area of the vessel, as is known in the art. Next, the user manipulates at least one of the retractable core wires 170 by retracting or extending the retractable core wire 170 within the core wire lumen 120 to impart an appropriate degree of stiffness to the shaft 140 to enable the catheter 100 to pass through the tortuous area. Highly tortuous areas require less stiff shafts. In examples in which the retractable core wire 170 has a tab 175, the tab 175 is manipulated to facilitate retraction or extension of the retractable core wire 170. Optionally, the retractable core wire 170 is retracted within the core wire lumen 120 or the retractable core wire 170 is removed from the core wire lumen 120. Optionally, the retractable core wire 170 is then extended within the core wire lumen 120 or is replaced within the core wire lumen 120 to re-establish stiffness to the shaft 140.

Figure 15:
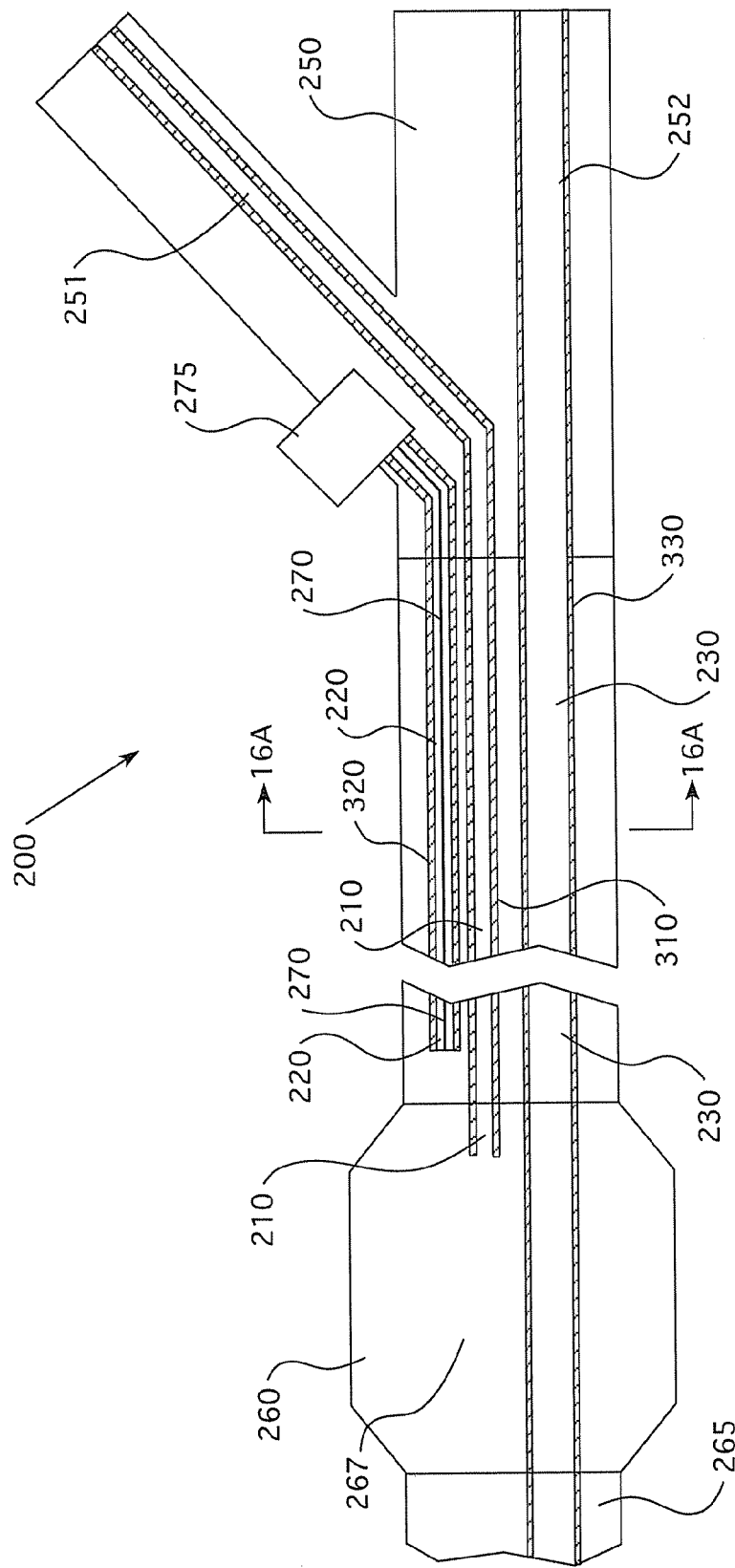
FIG. 15 is a longitudinal view of a section of an embodiment of a catheter having at least two tubular members.
Figure 16A:
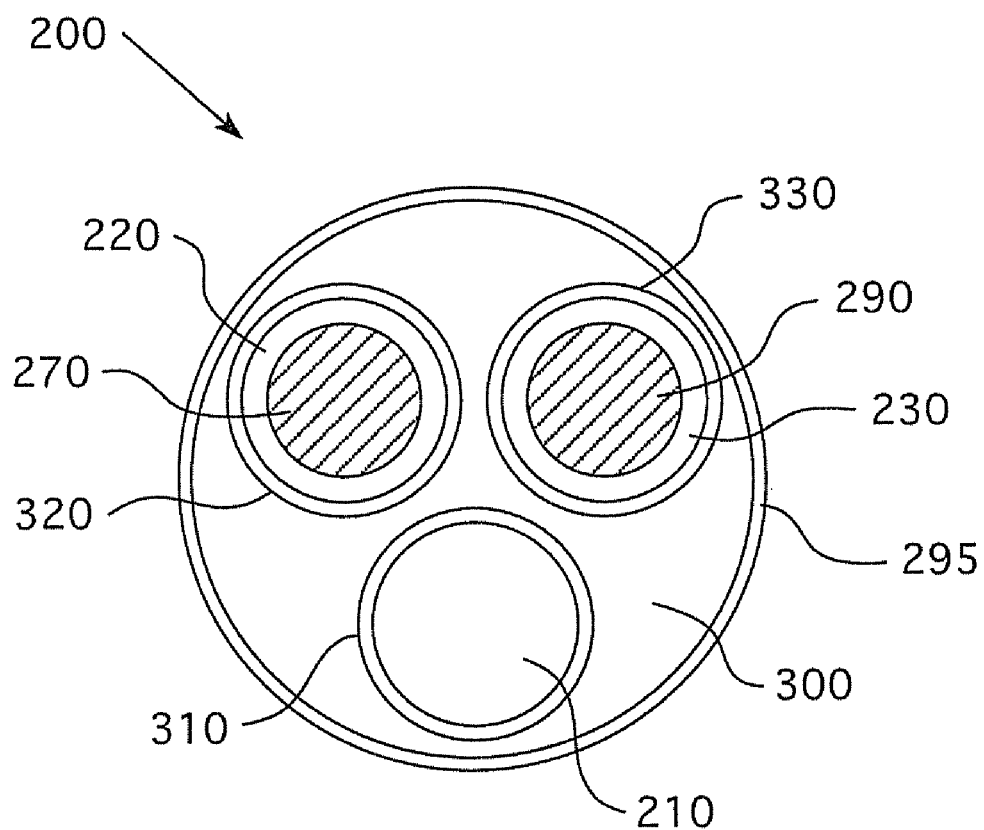
FIG. 16A is a cross-sectional view at line 16A-16A of the catheter of FIG. 15.
Figure 16B:
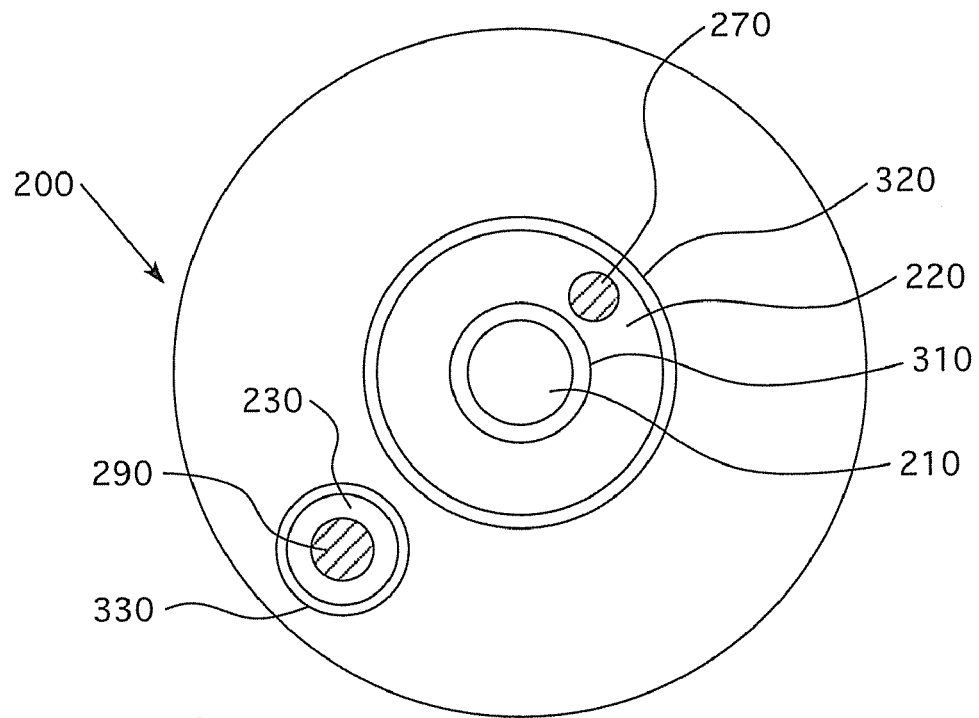
FIG. 16B is a cross-sectional view of an embodiment of the catheter with a second tubular member having a retractable core wire concentrically arranged around a first tubular member.
Figure 16C:
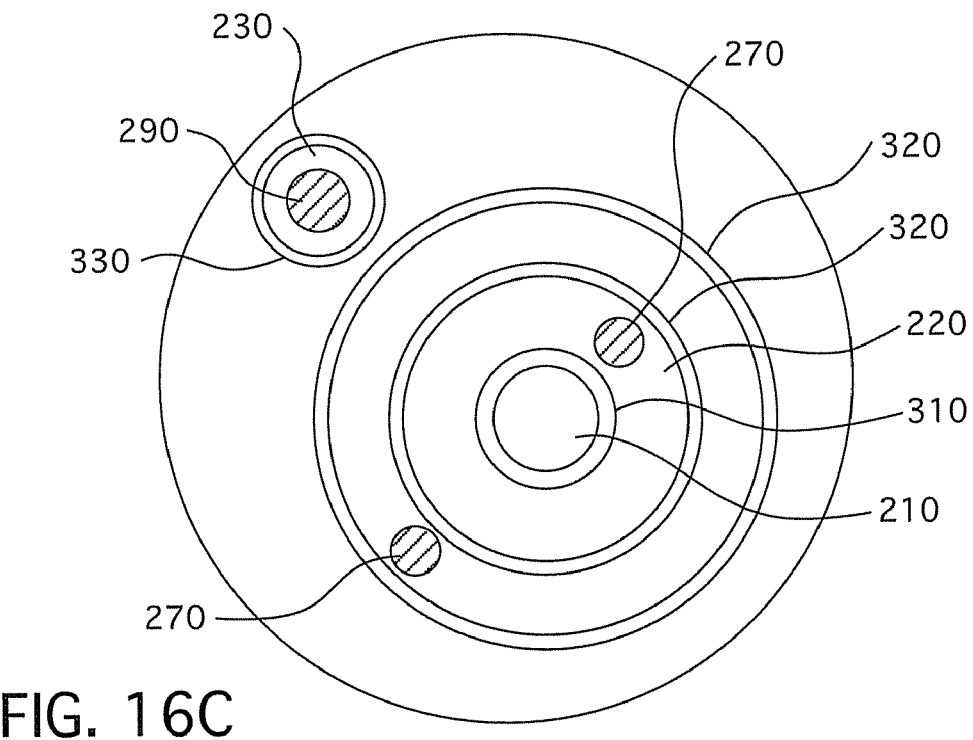
FIG. 16C is a cross-sectional view of an embodiment of the catheter with a plurality of second tubular members having retractable core wires concentrically arranged around the first tubular member.

In another embodiment shown in FIGS. 15 and 16, a catheter 200 has first and second tubular members 310, 320. The first tubular member 310 has a lumen 210, a proximal end configured for connection with a connector 250, a distal end configured for connection with an inflatable balloon 260, and a length defined by the proximal and distal ends. The second tubular member 320 has a lumen 220 configured for disposal of the retractable core wire 270. In an example, first and second tubular members 310, 320 are substantially parallel as shown in FIG. 16A. In an example, there is at least one second tubular member 320 concentrically arranged around the first tubular member 310 as shown in FIGS. 16B and 16C. The retractable core wire 270 has a length defined by proximal and distal ends as described above. The retractable core wire 270 has a substantially stiff member (not shown) and a tab 275 coupled to the distal end of the substantially stiff member that facilitates retraction and extension of the substantially stiff member within the lumen 220 of the second tubular member 320. In an example, the length of the member of the retractable core wire 270 is substantially equal to or less than a length of the lumen of the second tubular member 320. The substantially stiff member has an outer diameter that is less than an inner diameter of the lumen 220 of the second tubular member 320. A third tubular member 330 has a lumen 230 configured for the disposition of a guidewire 290 therein. In an alternate embodiment, the third tubular member is positioned coaxially within the first tubular member (not shown) similar to FIG. 9. Optionally, a sheath 295 surrounds the tubular members.

The catheter 200 also has a connector 250 having an inflation channel 251 that is in fluid communication with the lumen 210 of the first tubular member 310 at the proximal end of the first tubular member and a guidewire channel 252 that is in fluid communication with the lumen 230 of the third tubular member 330. In an example, a core wire channel is configured to receive the retractable core wire 270 and is in fluid communication with lumen 220 of the second tubular member 320 as described above (not shown). The distal end of the first tubular member 310 is in fluid communication with an inflatable balloon 260. The catheter 200 also has a distal flexible tip 265 that is configured for insertion into a vessel as described below. In examples, the catheter 200 has a low profile bond between at least one of the shaft 240, the stem 267, and the tip 265, as described in detail above.

The catheters embodied herein can be manufactured in a variety of ways, including but not limited to the following examples. In one example, the catheter can be manufactured by means of co-extrusion where a lubricious material is extruded to line the inner surface of the device lumens, such as Rilsan® nylon co-extruded inside Pebax® nylon. In another example, the catheter is manufactured using a heat expandable tubing comprised of a lubricious material. The lubricious material would be inserted into the device lumen(s) in a non-expanded state. Once positioned within the lumen (s), heat would be applied to the lubricious material and/or the device causing the lubricious material to expand to cover the inner surface of the device lumen(s). In yet another example, the catheter is manufactured by dipping the device into a lubricious material to coat the inner surface of the device lumen(s). The outer surface of the device would be covered to avoid coating the entire device. The device would then be submerged into a lubricious material which would coat the un-covered surfaces, the device lumen(s), with the lubricious material. Another example includes manufacturing the catheter by blow molding where the lubricious material, in a contracted tubular state, would be inserted into the lumen(s) of the device and hot air would be injected through the lubricious material causing it to expand to cover the inner surface of the device lumen(s).

While the foregoing has been set forth in considerable detail, it is to be understood that the drawings, detailed embodiments, and examples are presented for elucidation and not limitation. Design variations, especially in matters of shape, size, and arrangements of parts, may be made but are within the principles of the present disclosure. Those skilled in the art will realize that such changes, modifications, or combinations of elements, variations, equivalents, or improvements therein are still within the scope of the disclosure as defined in the appended claims.

We claim:

1. A catheter comprising:
   a connector having an inflation channel and a guidewire channel;
   a shaft joined at a proximal end to the connector and having an inflation lumen that is in fluid communication with the inflation channel, at least one core wire lumen concentrically positioned around the inflation lumen, and a guidewire lumen configured for disposition of a guidewire therein and in fluid communication with the guidewire channel;
   at least one retractable core wire disposed within the at least one core wire lumen, wherein the at least one retractable core wire has an outer diameter that is smaller than an inner diameter of the at least one lumen into which the core wire is disposed, and wherein the retractable core wire comprises a substantially stiff member having proximal and distal ends and a length defined by the ends that is substantially equal to or less than a length of the core wire lumen;
   a stem having a stem guidewire lumen portion configured for disposition of the guidewire therein and in fluid communication with the guidewire lumen;
   a tip having a tip guidewire lumen portion configured for disposition of the guidewire therein and in fluid communication with the stem guidewire lumen portion; and
   an inflatable balloon positioned substantially around the exterior of the stem, having proximal and distal ends, and that is in fluid communication with the inflation lumen.

2. The catheter as in claim 1, wherein the stem further comprises at least one stem core wire lumen portion configured for disposition of the core wire therein and in fluid communication with the at least one core wire lumen of the shaft.

3. The catheter as in claim 2, wherein the tip further comprises at least one tip core wire lumen portion configured for disposition of the core wire therein and in fluid communication with the at least one stem core wire lumen portion.

4. The catheter as in claim 1, wherein the connector further comprises a core wire channel that is in fluid communication with the core wire lumen, that is capable of receiving at least a proximal portion of the retractable core wire, and that is configured for retraction and extension of the retractable core wire therethrough.

5. The catheter as in claim 1, wherein the retractable core wire further comprises a tab connected to at least one of the proximal end and a proximal portion of the substantially stiff member, wherein the tab is configured for manipulation of the retractable core wire to retract the core wire in a proximal direction and to extend the core wire in a distal direction to vary the stiffness of the catheter.

6. The catheter as in claim 5, wherein the tab is at least one of an integrated tab that is integral with a portion of the connector, a detachable tab that is detachable from the connector, and a tab having a member that is configured for insertion into a substantially complementary slot in the connector.

7. The catheter as in claim 1, wherein the retractable core wire is removable.

8. The catheter as in claim 1, wherein the lumens are spaced apart.

9. The catheter as in claim 8 wherein one of the lumens is positioned substantially concentric to the other lumens.

10. The catheter as in claim 1, comprising at least two retractable core wires, wherein each core wire is disposed into the core wire lumens and wherein the retractable core wires have different stiffnesses.

11. The catheter as in claim 1 wherein at least two lumens are substantially parallel to each other.

12. The catheter as in claim 1 wherein the member is at least one of substantially elongate, substantially helical, substantially tapered, and substantially coiled with a solid substantially tapered inner core.

13. The catheter as in claim 1 wherein the member is made from at least one material selected from the group consisting of stainless steel, nitinol, and plastic.

14. The catheter as in claim 1 wherein at least one of the shaft, stem, tip, member, and lumen is at least one of formed from, co-extruded with, and coated with a lubricious material or a hydrophilic material.

15. The catheter as in claim 14 wherein the lubricious material is selected from the group consisting of nylon, Rilsan®, nylon, polytetrafluoroethylene (PTFE), PEBAX® material, polyether ether ketone (PEEK), polyimide, polyethylene of varying densities, polyethylene terephthalate (PET), polyurethane (PU), high density polyethlyene (HDPE), and fluorinated ethylene propylene.

16. The catheter as in claim 1, wherein at least one of the shaft, at least one of the lumens, and the core wire are tapered in diameter.

17. The catheter as in claim 1, wherein the catheter is an over-the-wire catheter.

18. The catheter as in claim 1, wherein the catheter is a rapid exchange catheter.

19. The catheter as in claim 1, wherein a distal portion of the shaft has a recess that extends around a circumference thereof and that is substantially flush with a second recess that extends around a circumference of a proximal portion of the stem around which the inflation balloon is positioned to form a first junction, and wherein a distal portion of the stem has a third recess that extend s around a circumference thereof that is substantially flush with a fourth recess that extends around a circumference of a proximal portion of the tip to form a second junction, wherein the junctions have a substantially low profile and wherein proximal and distal ends of the balloon are secured in the junctions.

20. The catheter as in claim 19, wherein the junctions have a substantially zero profile.

21. A catheter comprising:
a connector having at least one of an inflation channel, at least one core wire channel, and a guidewire channel;
an inflatable balloon having proximal and distal ends;
a flexible tip;
at least one retractable core wire comprising a substantially stiff member having proximal and distal ends;
a first tubular member configured for connection at a proximal end with the connector and having a lumen in fluid communication with the inflation channel of the connector and the balloon, and configured for connection at a distal end with the inflatable balloon;
at least one second tubular member configured for connection at a proximal end with the connector and having a lumen configured for disposition of the retractable core wire therein and in fluid communication with the core wire channel of the connector, wherein a length of the retractable core wire is substantially equal to or less than a length of the lumen of the second tubular member; and wherein at least one second tubular member is substantially concentrically positioned around the first tubular member;
a third tubular member having a lumen in fluid communication with the guidewire channel of the connector and configured for connection at a proximal end with the connector and for disposition of a guidewire therein; and
a sheath surrounding the tubular members.

22. The catheter as in claim 21, wherein the retractable core wire further comprises a tab coupled to at least one of the proximal end and a proximal portion of the substantially stiff member, wherein the tab facilitates retraction and extension of the member within the lumen of the second tubular member.

23. The catheter as in claim 21, wherein at least one of the tubular members, lumens, and retractable core wire is at least one of formed from, co-extruded with, or coated with a lubricious material or a hydrophilic material.

24. The catheter as in claim 23, wherein the lubricious material is selected from the group consisting of nylon, Rilsan®, nylon, polytetrafluoroethylene (PTFE), PEBAX® material, polyether ether ketone (PEEK), polyimide, polyethylene of varying densities, polyethylene terephthalate (PET), polyurethane (PU), high density polyethlyene (HDPE), and fluorinated ethylene propylene.

25. The catheter as in claim 21, wherein the tubular members are substantially parallel to each other.

26. The catheter as in claim 21, wherein at least one of the second tubular member and the core wire is at least one of substantially elongate, substantially helical, substantially tapered, and substantially coiled.

27. The catheter as in claim 21, wherein at least one second tubular member extends at least partially through the stem or tip.

* * * * *

UNITED STATES PATENT AND TRADEMARK OFFICE
CERTIFICATE OF CORRECTION

PATENT NO. : 8,267,886 B2
APPLICATION NO. : 12/339686
DATED : September 18, 2012
INVENTOR(S) : Ewing et al.

It is certified that error appears in the above-identified patent and that said Letters Patent is hereby corrected as shown below:

On the Title Page, in item (75), under "Inventors", delete "GREGORY A. BRUCKER" and insert -- GREGORY G. BRUCKER --, therefor.

On the Title Page, in item (73), under "Assignee", delete "MEDRAD, INC." and insert -- BAYER PHARMA AG CORPORATION --, therefor.

In Claim 14, Column 11, Line 49, delete "and lumen," and insert -- and one or more lumens --, therefor.

In Claim 27, Column 12, Lines 64-65, delete "through the stem or tip," and insert -- through a stem or the tip --, therefor.

Signed and Sealed this
Nineteenth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,267,886 B2  
APPLICATION NO. : 12/339686  
DATED : September 18, 2012  
INVENTOR(S) : Ewing et al.

Page 1 of 1

It is certified that error appears in the above-identified patent and that said Letters Patent is hereby corrected as shown below:

IN THE CLAIMS:

In Claim 19, Column 12, Line 10, delete "are secured in the junctions," and insert -- are secured in the first and second junctions --, therefor.

In Claim 21, Column 12, Line 14, delete "at least one of an inflation channel," and insert -- at least one inflation channel --, therefor.

In Claim 21, Column 12, Line 32, delete "wherein at least" and insert -- wherein the at least --, therefor.

Signed and Sealed this  
Ninth Day of July, 2013

Teresa Stanek Rea  
*Acting Director of the United States Patent and Trademark Office*